(12) United States Patent
Joziak et al.

(10) Patent No.: US 8,802,060 B2
(45) Date of Patent: Aug. 12, 2014

(54) FOAMABLE FLUORIDE ORAL CARE COMPOSITION

(75) Inventors: Marilou Theresa Joziak, South River, NJ (US); Steven Wade Fisher, Middlesex, NJ (US)

(73) Assignee: Colgate-Palmolive Company, New York, NY (US)

( * ) Notice: Subject to any disclaimer, the term of this patent is extended or adjusted under 35 U.S.C. 154(b) by 220 days.

(21) Appl. No.: 11/865,457

(22) Filed: Oct. 1, 2007

(65) Prior Publication Data

US 2009/0087391 A1    Apr. 2, 2009

(51) Int. Cl.
*A61K 8/00* (2006.01)
*A61Q 11/00* (2006.01)
*A61K 6/00* (2006.01)

(52) U.S. Cl.
USPC .............. 424/52; 424/49; 424/401; 433/215; 433/216

(58) Field of Classification Search
USPC ................. 424/49, 52, 401; 433/215, 216
See application file for complete search history.

(56) References Cited

U.S. PATENT DOCUMENTS

| | | | |
|---|---|---|---|
| 4,223,003 A | 9/1980 | Scheller | |
| 4,383,987 A * | 5/1983 | Kiozpeoplou | 424/49 |
| 4,528,182 A * | 7/1985 | Curtis et al. | 424/54 |
| 4,568,540 A | 2/1986 | Asano et al. | |
| 4,770,634 A | 9/1988 | Pellico | |
| 4,828,849 A | 5/1989 | Lynch et al. | |
| 5,071,637 A | 12/1991 | Pellico | |
| 5,073,363 A | 12/1991 | Pellico | |
| 5,180,577 A | 1/1993 | Polefka et al. | |
| 5,275,805 A | 1/1994 | Nabi et al. | |
| 5,599,526 A | 2/1997 | Viscio et al. | |
| 5,624,906 A * | 4/1997 | Vermeer | 514/23 |
| 5,723,105 A | 3/1998 | Viscio et al. | |
| 5,824,289 A | 10/1998 | Stoltz | |
| 6,142,338 A | 11/2000 | Pellicano | |
| 6,361,761 B1 | 3/2002 | Joziak et al. | |
| 6,622,943 B2 | 9/2003 | Poisson et al. | |
| 6,789,702 B2 | 9/2004 | O'Connor et al. | |
| 2004/0241099 A1 * | 12/2004 | Popp et al. | 424/45 |
| 2004/0247534 A1 * | 12/2004 | Stoltz | 424/52 |

FOREIGN PATENT DOCUMENTS

| | | |
|---|---|---|
| CN | 1794998 | 6/2006 |
| JP | H10-087456 | 4/1998 |
| JP | 10-139643 | 5/1998 |
| JP | H10-114636 | 5/1998 |
| JP | H10-114637 | 5/1998 |
| JP | 11-116451 | 4/1999 |
| JP | 2000-281156 | 10/2000 |
| JP | 2007-137773 A | 6/2007 |
| WO | 01/76533 A1 | 10/2001 |
| WO | WO 2006/073559 | 7/2006 |

OTHER PUBLICATIONS

International Search Report PCT/US2008/078091 mailed May 13, 2009.

* cited by examiner

*Primary Examiner* — Lezah Roberts
(74) *Attorney, Agent, or Firm* — Howard C. Lee

(57) ABSTRACT

A dental fluoride foam composition comprising an aqueous solution of a water soluble fluoride ion releasable salt, a surfactant selected from the group consisting of nonionic surfactants, zwitterionic surfactants, betaine surfactants and mixtures thereof; and an orally compatible acidifying agent in an amount sufficient to adjust the pH of the composition to about 3 to about 5. The composition is stable at low temperatures and is a clear solution substantially free of precipitates when held at 4.4° C. for 12 hours. When dispensed from a container into the trough of a dental tray, the composition forms a low density, rapidly collapsible foam which substantially liquefies in about 1 minute after being dispensed from the foam generating container and placed in contact with a patient's teeth.

23 Claims, No Drawings

FOAMABLE FLUORIDE ORAL CARE COMPOSITION

BACKGROUND OF THE INVENTION

Effective medical management of dental caries is required for populations of patients that exhibit increased risk factors for caries. It is known that the presence of dental caries in certain patient subpopulations accounts for a substantial proportion of the dental caries seen in the population at large. Reports exist indicating that in the United States, 25% of children account for 75% of dental caries.

One present practice to reduce dental caries in children is the periodic application, e.g., 1 to 2 times per year, of a foamable fluoride composition having a relatively high concentration of a fluoride releasing salt, e.g., 1-3% by weight sodium fluoride, that is packaged in an aerosol container in combination with an aerosol propellant. The composition is dispensed from the container into the trough of a dental tray as a dense, stable, non-flowable foam which is superimposed about and into engagement with the teeth to be treated, to affect fluoride uptake by the dental enamel.

Although conventional dental foams may be effective and are in present commercial use, in practice, the thick, dense foam that is produced may cause the patient to experience discomfort during treatment. Additionally, upon completion of treatment, the residual dense foam may be difficult and/or time consuming to remove from the patient's mouth. For at least these reasons, conventional foams may discourage professional usage and patient compliance with the fluoride treatment.

Therefore, what is needed in the art is an improved dental fluoride foam composition for the treatment of tooth surfaces that facilitates professional usage and patient compliance so that treatment can be repeated over time to provide effective fluoride treatment for dental caries.

The invention includes a low density foamable oral care composition comprising an aqueous solution of: a fluoride ion releasable salt; a surface active agent selected from the group consisting of nonionic surfactants, zwitterionic surfactants betaine surfactants, and mixtures thereof, and an acidifying agent in an amount sufficient to adjust the pH of the composition to about 3 to about 5, wherein the composition is substantially free of precipitates when maintained at a temperature of 4.4° C. (40° F.) for 12 hours.

Also included in the invention are related methods.

DETAILED DESCRIPTION OF THE INVENTION

The present invention provides foamable oral care compositions and methods of administration or application to, or use with, a human or other animal subject. As referenced herein, an "oral care composition" is any composition that is suitable for administration or application to the oral cavity of a human or animal subject for enhancing health, hygiene or appearance of the subject, preferably providing such benefits as the prevention or treatment of a physiologic condition or disorder, the provision of sensory, decorative or cosmetic benefits, and combinations thereof. In various embodiments, an oral care composition is not intentionally swallowed, but is rather retained in the oral cavity for a time sufficient to effect the intended utility. Preferably, specific materials and compositions to be used in this invention are, accordingly, pharmaceutically- or cosmetically-acceptable. As used herein, such a "pharmaceutically acceptable" or "cosmetically acceptable" component, or a component used in a "safe and effective amount", is one that is suitable for use with humans and/or animals to provide the desired therapeutic, prophylactic, sensory, decorative, or cosmetic benefit without undue adverse effects (such as toxicity, irritation, and allergic response) commensurate with a reasonable benefit/risk ratio.

In various embodiments, the present invention provides a low density, foamable, dental fluoride foam. In certain embodiments, the composition is packaged in a foam generating container. The composition comprises an aqueous solution of a water soluble fluoride ion releasable salt; a surfactant selected from the group consisting of nonionic surfactants, zwitterionic surfactants, betaine surfactants, and mixtures thereof; and an orally compatible acidifying agent in an amount sufficient to adjust the pH of the composition to about 3 to about 5. In one embodiment, the composition is a clear solution substantially free of precipitates when held at a temperature of 4.4° C. (40° F.) for 12 hours. The term "substantially free of precipitates" as used herein, means that the composition does not contain any precipitates that can be seen with the human eye, that is, without the aid of an artificial device.

In various embodiments, the composition has an upper solubility temperature greater than about 19.4° C. (85° F.), preferably greater than about 37.7° C. (100° F.), and a lower solubility temperature less than about 4.4° C. (40° F.), thus providing a stable and substantially clear solution. When dispensed from the container into the trough of a dental tray, the composition forms a low density, rapidly collapsible foam which substantially liquefies in about 1 minute, or less, after being dispensed from a foam generating container and placed in contact with a patient's teeth, from which it can be readily rinsed and removed from the patient's mouth.

The term "collapsible foam" as it is used in the present application means a foam that collapses, i.e. becomes substantially liquid in a period of no more than about 2 minutes after its formation in the dental tray trough and placement on the patient's teeth. After this short period of time, the aerosol foam is substantially collapsed to a liquid and the patient's teeth is simply rinsed free of the residual foam.

In various embodiments, the orally acceptable dentifrice carrier used to prepare the foamable oral composition comprises a water-phase. Water employed in the preparation of commercially suitable dental foams, toothpastes, gels, and mouthwashes should preferably be deionized and free of organic impurities. Water generally comprises of about 85% to 98%, preferably of about 90% to 95%, of the foamable dental fluoride compositions herein. In one embodiment, deionized water is provided at a level of about 91%. The water is free water which is added, plus that which is introduced with other materials and ingredients.

The water soluble fluoride ion releasable salt of the present invention is a fluoride ion source useful, for example, as an anticaries agent. The sources of fluoride ions, or fluoride-providing agents, may be slightly soluble in water or may be fully water-soluble. They are characterized by their ability to release fluoride ions in water, by their freedom from undesired reaction with other compounds of the oral preparation, and by their anticaries activity. Any orally acceptable fluoride ion source can be used. Non-limiting examples include soluble alkali metal or alkaline earth metal salts such as sodium fluoride, potassium fluoride, and calcium fluoride; ammonium fluoride; a copper fluoride such as cuprous fluoride; zinc fluoride, barium fluoride; sodium fluorosilicate; ammonium fluorosilicate; sodium fluorozirconate; sodium monofluorophosphate; aluminum mono- and di-fluorophosphate; and fluorinated sodium calcium pyrophosphate. Alkali metal and tin fluorides, such as sodium and stannous fluorides, indium fluoride, sodium monofluorophosphate (MFP), and mixtures thereof are preferred. In certain embodiments, amine fluorides are used, including olaflur (N'-octadecyltrimethylendiamine-N,N,N'-tris(2-ethanol)-dihydrofluoride).

The amount of fluoride-providing agent is dependent to some extent upon the type of compound, its solubility, and the type of oral preparation, but it must be a non-toxic amount. In various embodiments, water-soluble fluoride ion releasable salts are used and provided in a safe and effective amount. One or more fluoride ion sources are typically present in an amount that provides about 5,000 p.p.m to about 50,000 p.p.m. of fluoride ion, alternatively about 10,000 p.p.m. to about 30,000 p.p.m., or about 11,000 p.p.m., about 12,000 p.p.m., about 13,000 p.p.m., about 14,000 p.p.m. or about 17,000 p.p.m.

Surface active agents include components that may function as a surfactant, emulsifier, and/or foam modulator. Surface active agents generally increase prophylactic action by thoroughly dispersing the fluoride ions throughout the oral cavity. Suitable emulsifying agents include those that are reasonably stable and foam throughout a wide pH range. In addition, preferred surface active agents form stable compositions at low temperatures such as 4.4° C. (40° F.). This renders the instant compositions more cosmetically acceptable and increases the available of actives that remain in solution.

The organic surface-active material is preferably selected from nonionic and zwitterionic surfactants. Mixtures of surfactants can also be used. In certain embodiments, oral compositions contain one or more surfactants in the range of about 0.1% to about 3%, and preferably of about 0.6% to about 1.5%, wherein all percentages are by weight based on the total weight of the oral composition.

Suitable nonionic surfactants include ethylene oxide/propylene oxide block copolymers (e.g., Poloxamers or PLURONIC® surfactants); polyethylene oxide condensates of alkyl phenols; products derived from the condensation of ethylene oxide with the reaction product of propylene oxide and ethylene diamine; ethylene oxide condensates of aliphatic alcohols; long chain tertiary amine oxides; long chain tertiary phosphine oxides; long chain dialkyl sulfoxides; and condensates of sorbitan esters of fatty acids with ethylene oxide (polysorbates).

Non-limiting examples of sorbitan ester ethoxylates include sorbitan fatty acid esters with of about 20 to about 60 moles of ethylene oxide (e.g., the TWEEN® surfactants, a trademark of ICI Americas, Inc., Wilmington, Del., U.S.A.) Particularly preferred polysorbates are Polysorbate 20 (polyoxyethylene 20 sorbitan monolaurate, TWEEN® 20) and Polysorbate 80 (polyoxyethylene 20 sorbitan mono-oleate, TWEEN® 80).

Suitable poloxamer surfactants include poly(oxyethylene) poly(oxypropylene) block copolymers having an average molecular weight of about 3,000 to about 15,000. Intermediate average molecular weights may be of about 6,000 to about 15,000 with a preferred average molecular weight of about 10,000 to about 15,000. Such copolymers are known commercially by the non-proprietary name of poloxamers, the name being used in conjunction with a numeric suffix to designate the individual identification of each copolymer. Poloxamers have varying contents of ethylene oxide and propylene oxide, resulting in a wide range of chemical structures and molecular weights. One preferred poloxamer is Poloxamer 407, available, for example, under the tradename Pluronic F127 by BASF of Mount Olive, N.J., U.S.A.

Zwitterionic surface active agents can be broadly described as those containing both a negative and a positive charged group. In various embodiments, they are derivatives of aliphatic quaternary ammonium, phosphonium, and sulfonium compounds, in which the aliphatic radicals can be straight chain or branched of about 8 carbons or more, and preferably 8 to about 18 or 20 carbons. The positively charged group is typically a quaternary ammonium group, while the negatively charged group is generally an anionic water-solubilizing group such as carboxy, sulfonate, sulfate, phosphate or phosphonate. One example of a suitable of a suitable zwitterionic surfactant is 4-(N,N-di(2-hydroxyethyl)-N-octadecylammonio)-butane-1-carboxylate.

Another non-limiting example is betaine surfactants, such as those disclosed in U.S. Pat. No. 5,180,577, the disclosure of which is incorporated herein by reference. Preferred betaines include those derived structurally from N,N-dimethylglycine. They contain a quaternary nitrogen and a carboxylate group separated by a single methylene group. Typical alkyldimethyl betaines include decyl betaine, cocobetaine, myristyl betaine, palmityl betaine, lauryl betaine, cetyl betaine, stearyl betaine, and the like. Non-limiting examples of amidobetaines include cocoamidoethyl betaine, cocoamidopropyl betaine, lauramidopropyl betaine, and the like. To illustrate, amidopropyl betaines are represented by the formula;

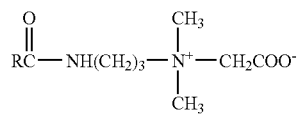

wherein RCO represents a fatty acid residue and R contains of about 6 to 24 carbon atoms or greater, preferably of about 8 to 20 carbon atoms, more preferably about 12 to 18 carbon atoms. Cocamidopropyl betaine is a preferred commercial embodiment where RCO is derived from coconut oil. In one embodiment, cocoamidopropyl betaine is present at a level of about 1%.

In various embodiments, the surfactants provide suitable foaming characteristics and have a Hydrophile-Lipophile Balance (HLB) value of at least 12. As is known in the art, HLB is an empirical expression for the relationship of the hydrophilic and hydrophobic groups of a surfactant. Preferably the HLB value of the surfactants used in the present invention is of about 14-30, more preferably of about 18-23. It should be understood, however, that it may be desirable to have an HLB value higher or lower to accommodate various compositions.

The present invention provides a stable oral composition that is clear in appearance and substantially free from precipitates. In various embodiments, the compositions are stable over a range of temperature about 4.4° C. (40° F.) to at least about 29.4° C. (85° F.), and more preferably to at least 100° F. Further, the compositions preferably remain stable in solution at low temperatures such as 40° F. for extended periods, such as 12 hours or more. In various embodiments, compositions further contain propellant gases such as those disclosed below, and maintain low temperature stability.

It is known that various surfactant solutions, including e.g., certain nonionic surfactants that are stable (i.e., soluble) at low temperatures, tend to cloud at some point as the temperature is raised. Likewise, other surfactants, including e.g., certain taurates and sulfates, that are soluble at room temperatures may cloud or precipitate at some point as the temperature is lowered. These precipitation temperatures, or cloud points, are characteristic properties of the surfactants and are typically measured with ASTM D 2004-65 (2003)

using 1% aqueous surfactant solutions. It can be appreciated that precipitation points, or cloud points, can also be measured on other surfactant solutions, including those formulated according to the present invention with a fluoride ion source and other additives. The cloud point is referred to as the solubility limit of the particular solution; it is the temperature above (for an upper limit) or below (for a lower limit) which an aqueous solution of a water-soluble surfactant becomes turbid. In various embodiments, the compositions exhibit an upper solubility temperature, or upper cloud point, greater than about 9.4° C. (85° F.), preferably greater than 37.7° C. (100° F.), and a lower solubility temperature, or lower cloud point, less than about 4.4° C. (40° F.), preferably less than about 10.6° C. (35° F.).

pH modifying agents among those useful herein include acidifying agents to lower pH, basifying agents to raise pH, and buffering agents to control pH within a desired range. For example, one or more compounds selected from acidifying, basifying and buffering agents can be included to provide a pH of about 2 to about 6, or in various embodiments of about 3 to about 5, of about 3 to about 4, and of about 3.5 to about 4. Any orally acceptable pH modifying agent can be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and mixtures thereof. Acidifying agents useful in the practice of the present invention include inorganic acids such as phosphoric acid, hydrochloric acid and hydrofluoric acid and organic acids such as malic acid, hydroxysuccinic acid, citric acid and tartaric acid and mixtures thereof. The acidifying agent is present in the foamable composition in an amount ranging of about 0.5 to about 3.5% by weight to adjust the pH to between about 3 to about 5. One or more pH modifying agents are optionally present in a total amount effective to maintain the composition in an orally acceptable pH range. In one embodiment, the malic acid is present at a level of about 3% by weight. In certain embodiments, a buffering salt, such as sodium hydrogen phosphate, is included in the compositions to inhibit tooth demineralization exposed to the acidified foam. Preferably the sodium hydrogen phosphate is provided such that the composition contains about 0.1M phosphate ions. In one embodiment, the sodium hydrogen phosphate is present at a level of about 1.4% (e.g. about 1.38%).

In certain embodiments, the rapidly collapsible fluoride dental foams contain a sweetening agent. Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones and mixtures thereof. Among these agents, sodium saccharinate may be mentioned by way of one presently preferred example. One or more sweeteners are optionally present in a total amount depending strongly on the particular sweetener(s) selected, but typically at levels of about 0.005% to about 5%, optionally about 0.1 to about 1%, preferably 0.25 and about 0.35% relative to the total weight of the composition. The foams may also contain preservatives such as sodium benzoate, methyl para-hydroxybenzoate, propyl para-hydroxybenzoate and the like in quantities of between 0.01 and 0.5% by weight relative to the total weight of the composition. In one embodiment, the sodium benzoate is present at a level of about 0.1%.

A flavoring substance in proportions of preferably between about 0.5 and about 5% relative to the total weight of the foam expelled from the aerosol device is generally present in the composition. Flavorants among those useful herein include any material or mixture of materials operable to enhance the taste of the composition. Any orally acceptable natural or synthetic flavorant can be used, such as flavoring oils, flavoring, aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, mandarin, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, $\alpha$-irisone, propenyl guaicthol, thymol, linalool, benzaldehyde, cinnamaldehyde, N-ethyl-p-menthan-3-carboxamine, N,2,3-trimethyl-2-isopropylbutanamide, 3-1 menthoxypropane-1,2-diol, cinnamaldehyde glycerol acetal (CCA), methone glycerol acetal (MGA) and mixtures thereof. One or more flavorants are optionally present in a total amount of about 0.01% to about 5%, optionally in various embodiments about 0.05 to about 2%, and more preferably about 0.1 to about 1.5%, and about 0.5 to about 1.5%.

The propellants used in the pressurized aerosol container in which the foamable composition of the present invention may be packaged are selected from among compressed air, nitrous oxide, and carbon dioxide and, more typically a volatile hydrocarbon or mixture of volatile hydrocarbons (typically with 3 to 6 carbon atoms) having a vapor pressure of about 15 to about 80 psig, preferably about 30 to about 70 psig, at about 20° C. The term volatile hydrocarbons is also intended to include the halohydrocarbons. In certain embodiments, a particularly preferred propellant is the product sold by Diversified CPC International, Channahon, Ill., U.S.A. under the name Aeron A-46 ("A-46"). A-46 is a mixture of isobutane and propane with a vapor pressure of 46 psig at about 20° C. In certain embodiments, the propellant comprises about 75 to about 85 wt % propane and about 15 to about 25 wt % iso-butane. In various embodiments, the dental foam composition comprises about 5 to about 20 wt % of the compressed liquid propellant, more preferably about 7 to about 10 wt % of the propellant.

In various embodiments, the present invention may optionally use two propellants, referred to in the art as a dual-propellant system. The two main functions for the volatile propellant components are: (1) to propel the dentifrice from the dispensing container, and (2) to cause the dispensed composition to foam. In certain embodiments, the same propellant composition is used for both purposes, in other embodiments different propellants are used. The function of the latter propellant may alternatively be referred to as a blowing agent, or foaming agent. Blowing agents are added to the formulation to cause the formulation to foam and do not supply the major mechanical energy used to propel the dentifrice from its container.

Foam modulators optionally useful herein include materials operable to increase amount, thickness or stability of foam generated by the composition (e.g., dentifrice compositions) upon agitation. Any orally acceptable foam modulator can be used, including polyethylene glycols (PEGs), also known as polyoxyethylenes. High molecular weight PEGs are suitable, including those having an average molecular weight of about 200,000 to about 7,000,000, for example about 5,000 to about 5,000,000 or about 1,000,000 to about 2,500,000. One or more PEGs are optionally present in a total amount of about 0.1% to about 10%, more preferably of about 0.2% to about 5%, and even more preferably of about 0.25% to about 270.

Viscosity modifiers among those optionally useful herein include mineral oil, petrolatum, clays and organomodified clays, silica and mixtures thereof. In various embodiments, such viscosity modifiers are operable to inhibit settling or separation of ingredients or to promote redispersibility upon agitation of a liquid composition. One or more viscosity modifiers are optionally present in a total amount between about 0.01% to about 10%, more preferably between about 0.1% to about 5% by weight of the composition.

Colorants among those optionally useful herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, FD&C dyes, and mixtures thereof. One or more colorants are optionally present in a total amount of about 0.001% to about 20%, for example of about 0.01% to about 10% or of about 0.1% to about 5%.

The foamable fluoride compositions of the present invention are prepared by blending the fluoride salt and acidifying agent with the surfactant, sweetening agent, flavor and preservative in an aqueous solution. The resulting aqueous solution, containing about 85 to about 98% by weight water, and preferably about 90 to about 95% by weight water, is added in a predetermined amount to a foam generating container. For an aerosol container, an appropriate aerosol valve is securely fitted to the mouth of the container. The container is then charged through the aerosol valve with an aerosol propellant of about 4% to 10%, preferably 7% of the relative fill weight of the aerosol container. A dispensing actuator and spout assembly is then fitted onto the valve.

Suitable pressure differential dispensers for use with a dual-propellant system include those comprising a collapsible product-containing bag being disposed within a rigid container which contains a propellant fluid, commonly referred to as a bag-in-can assembly. As in known in the art with the use of such dispensing containers, operation of a manually actuated dispensing valve permits the release of the composition, the propellant fluid being separated from the product by the fluid impermeable bag. The fluid impermeable bag systems commonly include bags made of chemically inert polymers and those described in U.S. Pat. No. 6,622,943, to Poisson, et al., issued Sep. 23, 2003 and U.S. Pat. No. 6,789,702, to O'Conner et al., issued Sep. 14, 2004.

In use, the foam generating container is shaken well and rotated to align the dispensing spout with the trough of a dental tray. The actuator is pressed to dispense an amount of fluoride foam that substantially fills the volume defined by the trough. The tray is then placed in a patient's mouth so as to superimpose the trough and its fluoride foam content about and into engagement with the teeth to be treated. The fluoride foam is maintained in engagement with the teeth for about 1 to 4 minutes to effect the fluoride treatment of the teeth.

The foam that is formed in the trough is "fluffy", with a relatively light body, as distinguished from the common dense foam, and collapses readily so as to allow for quick and easy removal of the residual treatment foam by simple aspiration or water rinsing of the mouth. The foam, upon dispensing, may exist in foam form for about 2 minutes, about 100 seconds, about 90 second before collapsing or liquefies.

The following examples are illustrative of the present invention and are not to be construed as a limitation of the invention as many variations are possible without departing from its spirit and scope.

EXAMPLE 1

A foamable fluoride treatment composition having the ingredients listed in Table 1 is prepared by dissolving the ingredients in water, in the order listed, at room temperature.

TABLE 1

| Ingredient | % |
| --- | --- |
| Deionized Water | 90.92 |
| Sodium fluoride | 2.65 |
| Sodium benzoate | 0.10 |
| Sodium phosphate monobasic | 1.38 |
| Sodium saccharin | 0.35 |
| Flavor | 0.60 |
| Malic Acid | 3.00 |
| Cocamidopropyl betaine (30% solution) | 1.00 |
| Total | 100.00 |

139.5 grams of the treatment composition and 10.5 grams of Aeron A-46, a 80/20 mixture of isobutane and propane, are introduced into an aerosol container equipped with a valve and nozzle. The composition is placed in a 4.4° C. (40° F.) refrigerator for at least 12 hours, and the resulting composition is clear, not cloudy, and does not have any visible precipitated particles. A dental foam dispensed from the container collapses within 1 minute after being dispensed into the trough of a dental tray when placed in contact with a patient's teeth. Upon collapse of the foam, the tray is removed from the patient's mouth and any residual foam is removed by simple water rinsing of the patient's mouth.

EXAMPLE 2

A foamable fluoride treatment composition having the ingredients listed in Table 2 is prepared by dissolving the ingredients in water, in the order listed, at room temperature by the method described previously in Example 1. However, in the present example, the surfactant comprises Pluronic F-127, and no cocamidopropyl betaine is added to the composition. This composition is similarly placed in a 4.4° C. (40° F.) refrigerator for at least 12 hours, and the resulting composition is clear, not cloudy, and does not have any visible precipitated particles.

TABLE 2

| Ingredient | % |
| --- | --- |
| Deionized Water | 90.92 |
| Sodium fluoride | 2.65 |
| Sodium benzoate | 0.10 |
| Sodium phosphate monobasic | 1.38 |
| Sodium saccharin | 0.35 |
| Flavor | 0.60 |
| Malic Acid | 3.00 |
| Pluronic F-127 | 1.00 |
| Total | 100.00 |

EXAMPLE 3

A foamable fluoride treatment composition having the ingredients listed in Table 3 is prepared by dissolving the ingredients in water, in the order listed, at room temperature by the method described previously in Example 1. However, in the present example, the surfactant comprises sodium lauryl sulfate, and no Pluronic F-127 or cocamidopropyl betaine is added to the composition. This composition is similarly placed in a 4.4° C. (40° F.) refrigerator for at least 12 hours, and the resulting composition is cloudy, and does not have visible precipitated particles.

TABLE 3

| Ingredient | % |
| --- | --- |
| Deionized Water | 90.92 |
| Sodium fluoride | 2.65 |
| Sodium benzoate | 0.10 |
| Sodium phosphate monobasic | 1.38 |
| Sodium saccharin | 0.35 |
| Flavor | 0.60 |
| Malic Acid | 3.00 |
| Sodium lauryl sulfate | 1.00 |
| Total | 100.00 |

What is claimed is:

1. A foamable oral care composition comprising an aqueous solution of:
   a surface active agent selected from the group consisting of zwitterionic surfactants, betaine surfactants, and mixtures thereof, said surface active agent is being present in an amount from 0.1% to 1.5% by weight; and
   an acidifying agent comprising malic acid in an amount sufficient to adjust the pH of the composition to about 3 to about 5,
   wherein the composition is clear when maintained at a temperature of 4.4° C. (40° F.) for 12 hours and
   wherein the composition, when dispensed, forms a foam that collapses within less than 120 seconds.

2. The composition of claim 1 further comprising a fluoride ion releasable salt.

3. The composition of claim 1, packaged in a foam generating container.

4. The composition of claim 3, wherein the composition, when dispensed from the container, forms a foam that liquefies in about 1 minute.

5. The composition of claim 2, wherein the fluoride ion releasable salt is present in an amount that provides about 12,000 p.p.m of fluoride ion.

6. The composition of claim 1, wherein the surface active agent is an amido betaine surfactant.

7. The composition of claim 1, wherein the surface active agent is cocamidopropyl betaine.

8. The composition of claim 1, wherein the fluoride ion releasable salt is sodium fluoride.

9. The composition of claim 3, wherein the foam generating container is an aerosol container.

10. The composition of claim 3, wherein the foam generating container is a bag-in-can assembly.

11. The composition of claim 9, wherein the aerosol container is charged with a hydrocarbon gas.

12. The composition of claim 11, wherein the hydrocarbon gas comprises a mixture of isobutene and propane.

13. The composition of claim 1, further comprising polyethylene glycol.

14. The composition of claim 1, wherein the surface active agent has an HLB value greater than 12.

15. The composition of claim 1, wherein the surface active agent has an HLB value of about 18 to about 23.

16. The composition of claim 1, further comprising sodium hydrogen phosphate.

17. A foamable dental fluoride composition packaged in a foam generating container, the composition comprising an aqueous solution of:
    a water soluble fluoride ion releasable salt;
    a surface active agent selected from the group consisting of zwitterionic surfactants, betaine surfactants, and mixtures thereof, said surface active agent being present in an amount from 0.1% to 1.5% by weight; and
    an orally compatible acidifying agent comprising malic acid in an amount sufficient to adjust the pH of the composition to about 3 to about 5,
    wherein the composition when dispensed from the container into the trough of a dental tray forms a rapidly collapsible foam that liquefies in about 1 minute after being dispensed from the foam generating container and placed in contact with a patient's teeth,
    further wherein the composition is stable and clear for at least 12 hours at 4.4° C. (40° F.).

18. The composition of claim 17, wherein the surface active agent comprises a betaine surfactant.

19. The composition of claim 18, wherein the betaine surfactant comprises cocamidopropyl betaine.

20. The composition of claim 17, wherein the surface active agent further comprises a poloxamer surfactant.

21. The composition of claim 17, wherein the fluoride salt comprises sodium fluoride.

22. The composition of claim 17, wherein the foam generating container is an aerosol container charged with a hydrocarbon gas.

23. The composition of claim 22, wherein the hydrocarbon gas comprises a mixture of isobutene and propane.

* * * * *